(12) United States Patent
Marat et al.

(10) Patent No.: US 8,617,524 B2
(45) Date of Patent: *Dec. 31, 2013

(54) DEPIGMENTING KERATIN MATERIALS UTILIZING DITHIOLANE COMPOUNDS

(75) Inventors: Xavier Marat, Paris (FR); Karine Lucet-Levannier, Rueil-Malmaison (FR); Laurent Marrot, Livry Gargan (FR)

(73) Assignee: L'Oreal, Paris (FR)

( * ) Notice: Subject to any disclaimer, the term of this patent is extended or adjusted under 35 U.S.C. 154(b) by 626 days.

This patent is subject to a terminal disclaimer.

(21) Appl. No.: 12/591,714

(22) Filed: Nov. 30, 2009

(65) Prior Publication Data

US 2010/0135942 A1 Jun. 3, 2010

Related U.S. Application Data

(60) Provisional application No. 61/193,507, filed on Dec. 4, 2008.

(30) Foreign Application Priority Data

Nov. 28, 2008 (FR) ...................................... 08 58075

(51) Int. Cl.
*A61K 8/49* (2006.01)
*A61Q 5/08* (2006.01)

(52) U.S. Cl.
USPC ................... 424/62; 424/59; 424/60; 424/69; 514/938; 514/944

(58) Field of Classification Search
USPC ................... 424/59, 60, 62, 69; 514/938, 944
See application file for complete search history.

(56) References Cited

U.S. PATENT DOCUMENTS

| | | | | |
|---|---|---|---|---|
| 4,990,330 A | * | 2/1991 | Oyama | 424/59 |
| 6,313,164 B1 | * | 11/2001 | Fujita et al. | 514/440 |
| 2010/0197759 A1 | * | 8/2010 | Marat et al. | 514/422 |

FOREIGN PATENT DOCUMENTS

| | | | |
|---|---|---|---|
| EP | 0308919 A1 | | 3/1989 |
| JP | 009012471 A | * | 1/1997 |
| JP | 2006-206513 | * | 10/2006 |
| WO | WO 98/23606 | * | 6/1998 |

OTHER PUBLICATIONS

Kurobe et al., "Preparation and formulation of cyclic dithio derivatives as remedies for diabetic kidney diseases, and lenitives for digestive disorders" CAPLUS, Jun. 4, 1988.

* cited by examiner

*Primary Examiner* — Ernst Arnold
*Assistant Examiner* — Hong Yu
(74) *Attorney, Agent, or Firm* — Buchanan Ingersoll & Rooney PC

(57) ABSTRACT

A cosmetic regime or regimen for depigmenting, lightening and/or bleaching keratin materials, especially the skin, entails topically applying thereon a cosmetic composition containing a dithiolane compound of formula (I):

in which:
  Y is O, $NR_1$ or S
  $R_1$ is a hydrogen atom; a $C_1$-$C_{20}$ alkyl radical or an optionally substituted phenyl radical;
  R is a hydrogen atom; or a $C_1$-$C_{20}$ alkyl radical, or an optionally substituted phenyl radical, or a $C_1$-$C_8$ alkyl radical containing an optionally substituted phenyl substituent;
  n=0 or 1 or 2;
and also the salts, chelates, solvates and optical isomers thereof.

11 Claims, No Drawings

DEPIGMENTING KERATIN MATERIALS UTILIZING DITHIOLANE COMPOUNDS

CROSS-REFERENCE TO PRIORITY/PROVISIONAL APPLICATIONS

This application claims priority under 35 U.S.C. §119 of FR 0858075, filed Nov. 28, 2008, and 35 U.S.C. §120 of U.S. Provisional Application No. 61/193,507, filed Dec. 4, 2008, each hereby expressly incorporated by reference and each assigned to the assignee hereof.

BACKGROUND OF THE INVENTION

1. Technical Field of the Invention

The present invention relates to a cosmetic treatment regime or regimen process especially for depigmenting and/or bleaching the skin, by application thereon of at least one compound of dithiolane type.

2. Description of Background and/or Related and/or Prior Art

The color of human skin depends on many factors and especially on the seasons of the year, race and sex; it is mainly determined by the nature and concentration of melanin produced by the melanocytes. Melanocytes are specialized cells that synthesize melanin, by means of particular organelles, the melanosomes. At different periods in their life, certain individuals develop darker and/or more colored marks on their skin and especially on the hands, giving the skin a heterogeneous appearance. These marks are also due to a large concentration of melanin in the keratinocytes located at the surface of the skin.

The administration of highly effective, harmless topical depigmenting substances is most particularly sought to treat regional hyperpigmentations caused by melanocyte hyperactivity, such as idiopathic melasmas, occurring during pregnancy ("pregnancy mask" or chloasma) or oestro-progestative contraception, localized hyperpigmentations caused by benign melanocytic proliferation and hyperactivity, such as senile pigmentation marks known as actinic lentigo, accidental hyperpigmentations, possibly due to post-lesional cicatrization or photosensitization, and also certain leukodermias, such as vitiligo. For the latter (cicatrizations that may result in a scar, giving the skin a whiter appearance), failing the possibility of repigmenting the damaged skin, depigmentation of the areas of residual normal skin is completed to impart to the skin as a whole a uniform white complexion.

The mechanism of formation of skin pigmentation, i.e., the formation of melanin, is particularly complex and schematically involves the following main steps:

Tyrosine->Dopa->Dopaquinone->Dopachrome->Melanin

Tyrosinase (monophenol dihydroxyl phenylalanine: oxygen oxidoreductase EC 1.14.18.1) is the essential enzyme participating in this sequence of reactions. It especially catalyzes the reaction for the conversion of tyrosine into dopa (dihydroxyphenylalanine) by virtue of its hydroxylase activity, and the reaction for the conversion of dopa into dopaquinone by virtue of its oxidase activity. This tyrosinase acts only when it is in the mature form, under the influence of certain biological factors.

A substance is recognized as being depigmenting if it acts directly on the vitality of the epidermal melanocytes in which melanogenesis takes place and/or if it interferes with one of the steps in the biosynthesis of melanin either by inhibiting one of the enzymes involved in melanogenesis or by inserting itself as a structural analogue of one of the chemical compounds of the melanin synthesis chain, which chain may then become blocked and thus ensure depigmentation.

The substances most commonly employed as depigmenting agents are, more particularly, hydroquinone and its derivatives, in particular its ethers such as hydroquinone monomethyl ether and monoethyl ether. Although they have a certain level of efficacy, these compounds are, unfortunately, not free of side effects on account of their toxicity, which may make them difficult or even hazardous to use. This toxicity arises from the fact that they participate in fundamental mechanisms of melanogenesis by killing cells which then run the risk of disturbing their biological environment and which consequently oblige the skin to eliminate them by producing toxins.

Thus, hydroquinone is a compound that is particularly irritant and cytotoxic to melanocytes, and whose total or partial replacement has been envisaged by many researchers.

Substances are thus sought, which do not participate in the melanogenesis mechanism, but which act upstream of tyrosinase by preventing its activation, and which are consequently much less toxic. Kojic acid, which complexes the copper present in the active site of tyrosinase, is commonly used as a tyrosinase activation inhibitor. Unfortunately, this compound is unstable in solution, which somewhat complicates the formulation of the composition.

Need continues to exist for a novel human skin-bleaching agent whose action is just as efficient as the known agents, but which does not have their drawbacks, i.e., which is non-irritant, non-toxic and/or non-allergenic to the skin, while at the same time being stable in a composition, or, alternatively, which has reinforced action so as to be able to be administered in smaller amount, which considerably reduces the observed side effects.

SUMMARY OF THE INVENTION

It has now surprisingly and unexpectedly been found that certain dithiolane compounds have good depigmenting activity, even at low concentration.

The present invention thus features a cosmetic regime or regimen for depigmenting, lightening and/or bleaching keratin materials, comprising the topical application thereon of a cosmetic composition which comprises, formulated into a physiologically acceptable medium, at least one compound of formula (I) as defined below.

The present invention also features the cosmetic administration of a compound of formula (I) as an agent for bleaching, lightening and/or depigmenting keratin materials.

This invention also features the formulation of a compound of formula (I) into dermatological compositions useful for depigmenting, lightening and/or bleaching keratin materials.

The compounds according to the invention promote the efficient depigmenting and/or lightening, or even the bleaching, of human skin. They are especially intended to be applied to the skin of individuals presenting brownish pigmentation marks or senescence marks, or to the skin of individuals who wish to combat the appearance of a brownish color arising from melanogenesis, for example following exposure to ultraviolet radiation.

Such compounds can also depigment and/or lighten bodily hair, the eyelashes, head hair, and also the lips and/or the nails.

The compounds according to the invention thus correspond to formula (I) below:

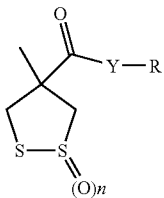

(I)

in which:

Y is O, $NR_1$ or S;

$R_1$ is a hydrogen atom, a saturated linear $C_1$-$C_{20}$ or branched $C_3$-$C_{20}$ or unsaturated $C_2$-$C_{20}$ alkyl hydrocarbon-based radical, a phenyl radical optionally substituted with one or more hydroxyl groups and/or with one or more $C_1$-$C_8$ alkoxy radicals;

R is a hydrogen atom, or a saturated linear $C_1$-$C_{20}$ or branched $C_3$-$C_{20}$ or unsaturated $C_2$-$C_{20}$ alkyl hydrocarbon-based radical, or a phenyl radical optionally substituted with one or more hydroxyl groups and/or with one or more $C_1$-$C_8$ alkoxy radicals, or a saturated $C_1$-$C_8$ alkyl radical containing a phenyl substituent optionally substituted with one or more hydroxyl groups and/or with one or more $C_1$-$C_8$ alkoxy radicals;

R optionally bears one or more substituents selected from among $OR_2$, $SR_2$, $NR_2R_3$, $COOR_2$ in which:

$R_2$ is a hydrogen atom or a saturated linear $C_1$-$C_5$ or branched $C_3$-$C_5$ or unsaturated $C_2$-$C_5$ hydrocarbon-based radical, or a phenyl radical;

$R_3$ is a hydrogen atom; a saturated linear $C_1$-$C_5$ or branched $C_3$-$C_5$ or unsaturated $C_2$-$C_5$ hydrocarbon-based radical, a phenyl radical, an acetyl group;

with the proviso that, when Y=$NR_1$, R and $R_1$ may form a ring member selected from among pyrrolidine, pyrroline, piperidine, piperazine, morpholine, thiomorpholine and azepine;

n=0 or 1 or 2, and also the salts, chelates, solvates and optical isomers thereof.

DETAILED DESCRIPTION OF BEST MODE AND SPECIFIC PREFERRED EMBODIMENTS THEREOF

The salts of the compounds of the present invention include conventional non-toxic salts of the said compounds, such as those formed from organic or mineral acids. Examples include the salts of mineral acids such as sulfuric acid, hydrochloric acid, hydrobromic acid, hydriodic acid, phosphoric acid or boric acid. Exemplary are the salts of organic acids, which may comprise one or more carboxylic, sulfonic or phosphonic acid groups. They may be linear, branched or cyclic aliphatic acids, or, alternatively, aromatic acids. These acids may also comprise one or more heteroatoms selected from among O and N, for example in the form of hydroxyl groups. Exemplary are propionic acid, acetic acid, terephthalic acid, citric acid and tartaric acid.

Exemplary are the salts of organic or mineral bases such as triethanolamine, aminopropanediol, sodium or zinc salts.

The solvates that are acceptable for the non-therapeutic administration of the compounds described in the present invention include conventional solvates such as those formed during the final step of preparation of the said compounds, due to the presence of solvents. Examples include the solvates due to the presence of water or of linear or branched alcohols such as ethanol or isopropanol.

The optical isomers are especially enantiomers and diastereoisomers.

The alkoxy radicals are preferentially linear $C_1$-$C_4$ radicals and more preferentially methoxy, ethoxy, propoxy or butoxy and even more preferentially methoxy.

Preferentially, the hydrocarbon-based radicals are linear or branched alkyls and may be selected from among: methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl.

Preferentially, the hydrocarbon-based radicals are saturated, linear or branched $C_1$-$C_8$ alkyl radicals: methyl, ethyl, propyl, isopropyl, butyl, isobutyl, tert-butyl, pentyl, hexyl, heptyl, octyl.

Preferably, the compounds of formula (I) are the following:

Y is S, O, $NR_1$;

$R_1$ is a hydrogen atom, a saturated linear $C_1$-$C_{10}$ or branched $C_3$-$C_{10}$ alkyl hydrocarbon-based radical;

R is a hydrogen atom, a saturated linear $C_1$-$C_{20}$ or branched $C_3$-$C_{20}$ alkyl hydrocarbon-based radical, a phenyl radical optionally substituted with one or more hydroxyl groups and/or with one or more $C_1$-$C_3$ alkoxy radicals, a saturated $C_1$-$C_5$ alkyl radical containing a phenyl substituent optionally substituted with one or more hydroxyl groups and/or with one or more $C_1$-$C_3$ alkoxy radicals; a linear $C_1$-$C_5$ alkyl hydrocarbon-based radical substituted with one or more identical or different groups selected from among $OR_2$, $SR_2$, $NR_2R_3$, $COOR_2$ in which:

$R_2$ is a hydrogen atom or a saturated linear $C_1$-$C_5$ or branched $C_3$-$C_5$ or unsaturated $C_2$-$C_5$ hydrocarbon-based radical, $R_3$ is a hydrogen atom, a saturated linear $C_1$-$C_5$ or branched $C_3$-$C_5$ hydrocarbon-based radical, a phenyl radical, or an acetyl radical;

with the proviso that, when Y=$NR_1$, R and $R_1$ may together form a pyrrolidine ring;

n=0 or 1 or 2;

and also the acid or base salts, chelates, solvates and optical isomers thereof.

Preferentially, the compounds of formula (I) are the following:

Y is O or $NR_1$;

$R_1$ is a hydrogen atom; a saturated linear $C_1$-$C_{10}$ or branched $C_3$-$C_{10}$ alkyl hydrocarbon-based radical;

R is a hydrogen atom; a saturated linear $C_1$-$C_{10}$ or branched $C_3$-$C_{10}$ alkyl hydrocarbon-based radical, a phenyl radical optionally substituted with one or more hydroxyl groups and/ or with one or more methoxy radicals, a saturated $C_1$-$C_3$ alkyl hydrocarbon-based radical containing a phenyl substituent optionally substituted with one or more hydroxyl groups and/ or with one or more methoxy radicals, a linear $C_1$-$C_4$ alkyl hydrocarbon-based radical substituted with one or more identical or different groups selected from among $OR_2$, $SR_2$, $NR_2R_3$, $COOR_2$ in which:

$R_2$ is a hydrogen atom or a saturated linear $C_1$-$C_5$ or branched $C_3$-$C_5$ hydrocarbon-based radical;

$R_3$ is a hydrogen atom; a saturated linear $C_1$-$C_5$ or branched $C_3$-$C_5$ hydrocarbon-based radical;

n=0 or 1 or 2;

and also the acid or base salts, chelates, solvates and optical isomers thereof.

More preferentially, the compounds of formula (I) are the following:

Y is $NR_1$;

$R_1$ is a hydrogen atom; a saturated linear $C_1$-$C_4$ alkyl hydrocarbon-based radical;

R is a hydrogen atom, a saturated linear $C_1$-$C_{10}$ or branched $C_3$-$C_{10}$ alkyl hydrocarbon-based radical; a phenyl radical; a saturated linear $C_1$-$C_4$ alkyl radical substituted with a phenyl optionally substituted with one or more identical or different groups selected from among OH, OMe, a linear $C_1$-$C_4$ alkyl hydrocarbon-based radical substituted with one or more identical or different groups selected from among OH, NHAc, $SR_2$, $COOR_2$ with $R_2$ being a hydrogen atom or a linear $C_1$-$C_4$ alkyl radical;

n=0 or 1 or 2;

and also the acid or base salts, chelates, solvates and optical isomers thereof.

Also preferentially, the compounds of formula (I) are the following:

Y is NH;

R is a hydrogen atom, a saturated linear $C_1$-$C_{10}$ or branched $C_3$-$C_{10}$ alkyl hydrocarbon-based radical, a phenyl radical, a saturated linear $C_1$-$C_4$ alkyl radical substituted with a phenyl optionally substituted with one or more identical or different groups selected from among OH, OMe, a linear $C_1$-$C_4$ alkyl hydrocarbon-based radical substituted with one or more identical or different groups selected from among OH, NHAc, $SR_2$, $COOR_2$ with $R_2$ being a hydrogen atom or a linear $C_1$-$C_4$ alkyl radical;

n=0 or 1 or 2;

and also the acid or base salts, chelates, solvates and optical isomers thereof.

Also preferentially, the compounds of formula (I) are the following:

Y is NH;

R is a hydrogen atom, a saturated linear $C_1$-$C_{10}$ or branched $C_3$-$C_{10}$ alkyl hydrocarbon-based radical;

n=0 or 1 or 2;

and also the acid or base salts, chelates, solvates and optical isomers thereof.

Preferentially, Y=O, $NR_1$.

More preferentially, Y=$NR_1$.

Even more preferentially, Y=NH.

Most preferentially, R=H or a $C_1$-$C_8$ alkyl radical.

Among the compounds of formula (I), the following compounds are preferred:

| No. | Structure | Chemical name |
|---|---|---|
| 1 | 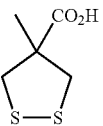 | 4-methyl-1,2-dithiolane-4-carboxylic acid |
| 2 | 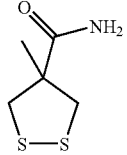 | 4-methyl-1,2-dithiolane-4-carboxamide |
| 3 | 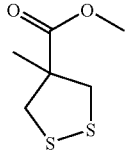 | methyl 4-methyl-1,2-dithiolane-4-carboxylate |
| 4 | 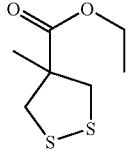 | ethyl 4-methyl-1,2-dithiolane-4-carboxylate |
| 5 | 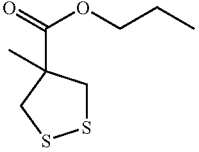 | propyl 4-methyl-1,2-dithiolane-4-carboxylate |

-continued

| No. | Structure | Chemical name |
|---|---|---|
| 6 | 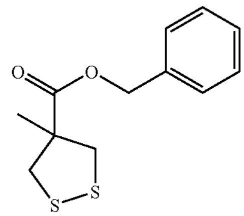 [SMILES: CC1(C(=O)OCc2ccccc2)CSSC1] | benzyl 4-methyl-1,2-dithiolane-4-carboxylate |
| 7 | 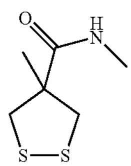 | N-methyl-4-methyl-1,2-dithiolane-4-carboxamide |
| 8 | 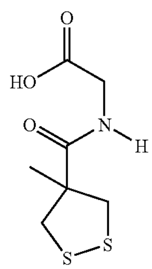 | {[(4-methyl-1,2-dithiolan-4-yl)carbonyl]amino} acetic acid |
| 9 | 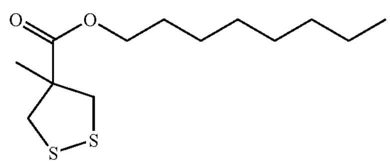 [SMILES: CCCCCCCCOC(=O)C1(C)CSSC1] | octyl 4-methyl-1,2-dithiolane-4-carboxylate |
| 10 | 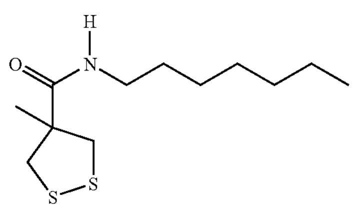 [SMILES: CCCCCCCNC(=O)C1(C)CSSC1] | N-heptyl-4-methyl-1,2-dithiolane-4-carboxamide |
| 11 | 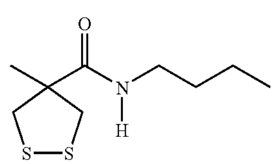 | N-butyl-4-methyl-1,2-dithiolane-4-carboxamide |
| 12 | 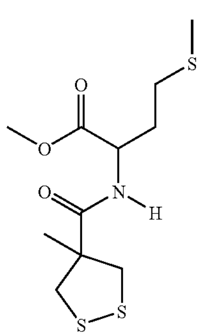 | methyl 2-{[(4-methyl-1,2-dithiolan-4-yl)carbonyl]amino}-4-(methylsulfanyl)butanoate |

| No. | Structure | Chemical name |
|---|---|---|
| 13 | 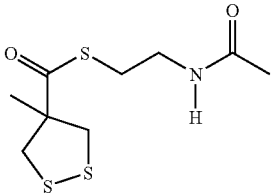 | S-[2-(acetylamino)ethyl] 4-methyl-1,2-dithiolane-4-carbothioate |
| 14 | 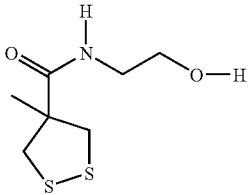 | N-(2-hydroxyethyl)-4-methyl-1,2-dithiolane-4-carboxamide |
| 15 | 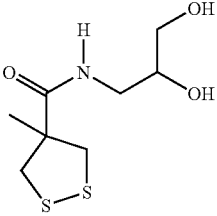 | N-(2,3-dihydroxypropyl)-4-methyl-1,2-dithiolane-4-carboxamide |
| 16 | 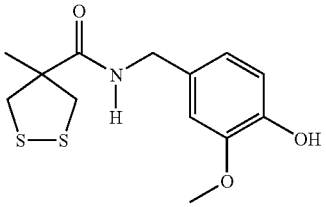 [SMILES: COc1cc(CNC(=O)C2(C)CSSC2)ccc1O] | N-(4-hydroxy-3-methoxybenzyl)-4-methyl-1,2-dithiolane-4-carboxamide |
| 17 | 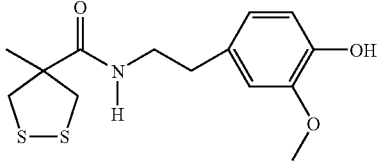 [SMILES: COc1cc(CCNC(=O)C2(C)CSSC2)ccc1O] | N-[2-(4-hydroxy-3-methoxyphenyl)ethyl]-4-methyl-1,2-dithiolane-4-carboxamide |
| 18 | 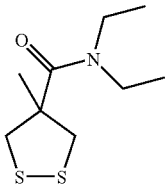 | N,N-diethyl-4-methyl-1,2-dithiolane-4-carboxamide |
| 19 | 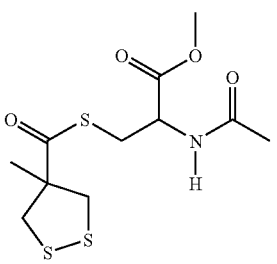 [SMILES: COC(=O)C(CSC(=O)C1(C)CSSC1)NC(C)=O] | methyl 2-(acetylamino)-3-{[(4-methyl-1,2-dithiolan-4-yl)carbonyl]sulfanyl}propanoate |

-continued

| No. | Structure | Chemical name |
|---|---|---|
| 20 | 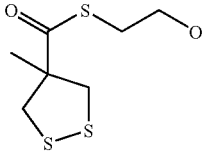 | S-(2-hydroxyethyl) 4-methyl-1,2-dithiolane-4-carbothioate |
| 21 | 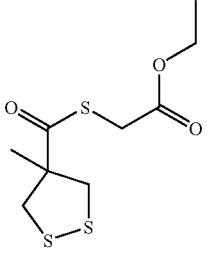 | ethyl {[(4-methyl-1,2-dithiolan-4-yl)carbonyl]sulfanyl}acetate |
| 22 | 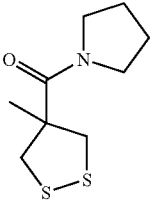 | [(4-methyl-1,2-dithiolan-4-yl)carbonyl]pyrrolidine |
| 23 | 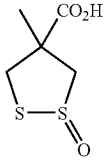 | 4-methyl-1,2-dithiolane-1-oxo-4-carboxylic acid |
| 24 | 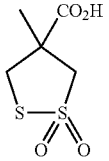 | 4-methyl-1,2-dithiolane-1,1-dioxo-4-carboxylic acid |
| 25 | 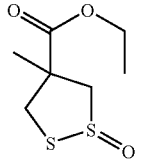 | ethyl 4-methyl-1,2-dithiolane-1-oxo-4-carboxylate |
| 26 | 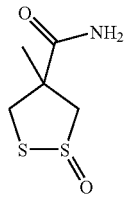 | 4-methyl-1,2-dithiolane-4-carboxamide 1-oxide |
| 27 | 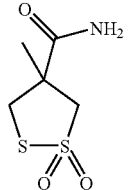 | 4-methyl-1,2-dithiolane-4-carboxamide 1,1-dioxide |

-continued

| No. | Structure | Chemical name |
|---|---|---|
| 28 | 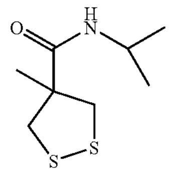 | 4-methyl-N-(1-methylethyl)-1,2-dithiolane-4-carboxamide |
| 29 | 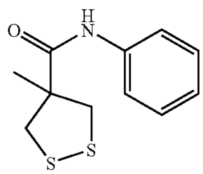 | 4-methyl-N-phenyl-1,2-dithiolane-4-carboxamide |
| 30 | 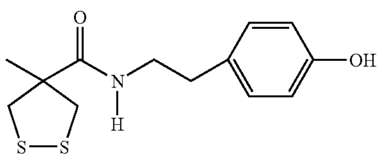 [SMILES: CC1(C(=O)NCCc2ccc(O)cc2)CSSC1] | N-[2-(4-hydroxyphenyl)ethyl]-4-methyl-1,2-dithiolane-4-carboxamide |
| 31 | 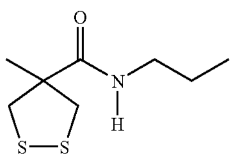 | N-propyl-4-methyl-1,2-dithiolane-4-carboxamide |
| 32 | 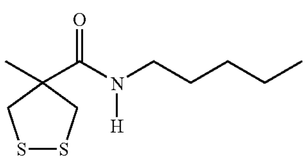 | N-pentyl-4-methyl-1,2-dithiolane-4-carboxamide |
| 33 | 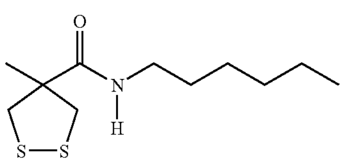 | N-hexyl-4-methyl-1,2-dithiolane-4-carboxamide |
| 34 | 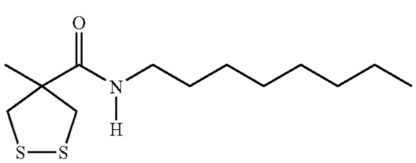 [SMILES: CCCCCCCCNC(=O)C1(C)CSSC1] | N-octyl-4-methyl-1,2-dithiolane-4-carboxamide |
| 35 | 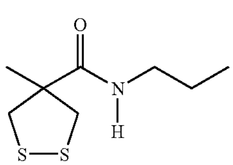 | N-propyl-4-methyl-1,2-dithiolane-4-carboxamide |
| 36 | 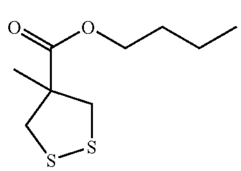 | butyl 4-methyl-1,2-dithiolane-4-carboxylate |

-continued

| No. | Structure | Chemical name |
| --- | --- | --- |
| 37 | 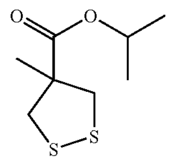 | isopropyl 4-methyl-1,2-dithiolane-4-carboxylate |
| 38 | 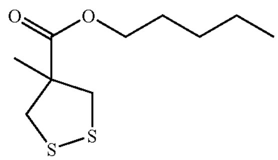 | pentyl 4-methyl-1,2-dithiolane-4-carboxylate |
| 39 | 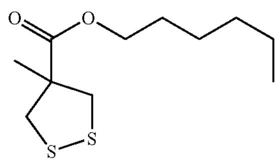 | hexyl 4-methyl-1,2-dithiolane-4-carboxylate |
| 40 | 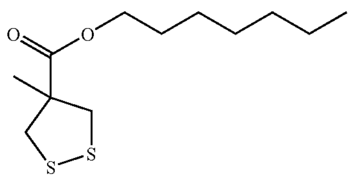 [SMILES: CCCCCCCOC(=O)C1(C)CSSC1] | heptyl 4-methyl-1,2-dithiolane-4-carboxylate |

Among these compounds, the following compounds are more particularly preferred:

| No. | Structure | Chemical name |
| --- | --- | --- |
| 2 | 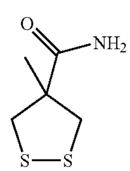 | 4-methyl-1,2-dithiolane-4-carboxamide |
| 10 | 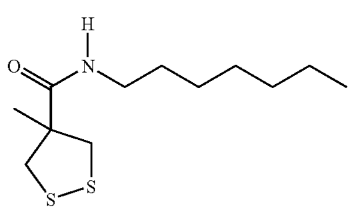 [SMILES: CCCCCCCNC(=O)C1(C)CSSC1] | N-heptyl-4-methyl-1,2-dithiolane-4-carboxamide |
| 11 | 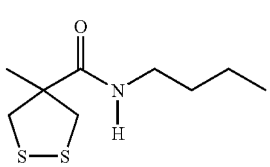 | N-butyl-4-methyl-1,2-dithiolane-4-carboxamide |

-continued

| No. | Structure | Chemical name |
|---|---|---|
| 26 | 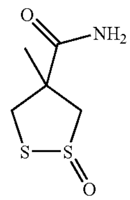 | 4-methyl-1,2-dithiolane-4-carboxamide 1-oxide |
| 27 | | 4-methyl-1,2-dithiolane-4-carboxamide 1,1-dioxide | and also the acid or base salts thereof, optical isomers thereof and solvates thereof.

Certain of the compounds in accordance with the invention are known per se. These are Compounds 1 to 8 below:

| No. | Structure | Chemical name | CAS |
|---|---|---|---|
| 1 | 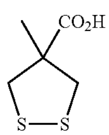 | 4-methyl-1,2-dithiolane-4-carboxylic acid | 208243-72-5 |
| 2 | 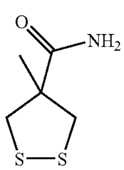 | 4-methyl-1,2-dithiolane-4-carboxamide | 208243-73-6 |
| 3 | 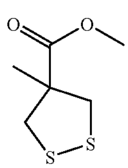 | methyl 4-methyl-1,2-dithiolane-4-carboxylate | 208243-88-3 |
| 4 | 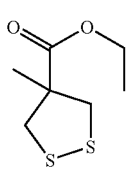 | ethyl 4-methyl-1,2-dithiolane-4-carboxylate | 208243-89-4 |
| 5 | 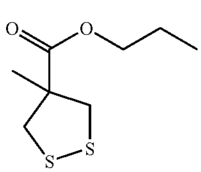 | propyl 4-methyl-1,2-dithiolane-4-carboxylate | 208243-90-7 |

| No. | Structure | Chemical name | CAS |
|---|---|---|---|
| 6 | 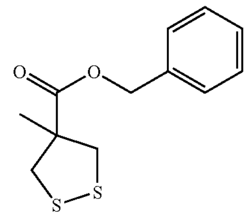 [SMILES: CC1(C(=O)OCc2ccccc2)CSSC1] | benzyl 4-methyl-1,2-dithiolane-4-carboxylate | 208243-73-6 |
| 7 | 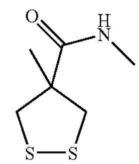 | N-methyl-4-methyl-1,2-dithiolane-4-carboxamide | 208243-91-8 |
| 8 | 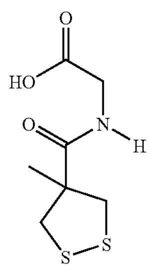 | {[(4-methyl-1,2-dithiolan-4-yl)carbonyl]amino}acetic acid | 208243-74-7 |

These compounds have been described in WO 98/23606 and administered in pharmacology as agents for reducing glucose or fat in the blood.

The compounds of formula (I) may be prepared according to one of the routes described below and documented in the review by Lene Teuber, Sulfur reports, 9(4), 257-349, 1990 Naturally occurring 1,2-dithiolanes and 1,2,3-trithianes. Chemical and Biological Properties, in EP-0,869,126 A1.

Starting with 2,2-bis(hydroxymethyl)propionic acid (CAS:4767-03-7), by functionalization of the hydroxyl groups to leaving groups X (alkyl or aryl sulfonates such as mesylates or tosylates, or halogens such as iodine, bromine or chlorine) followed by the introduction of sulfur according to the following reaction scheme:

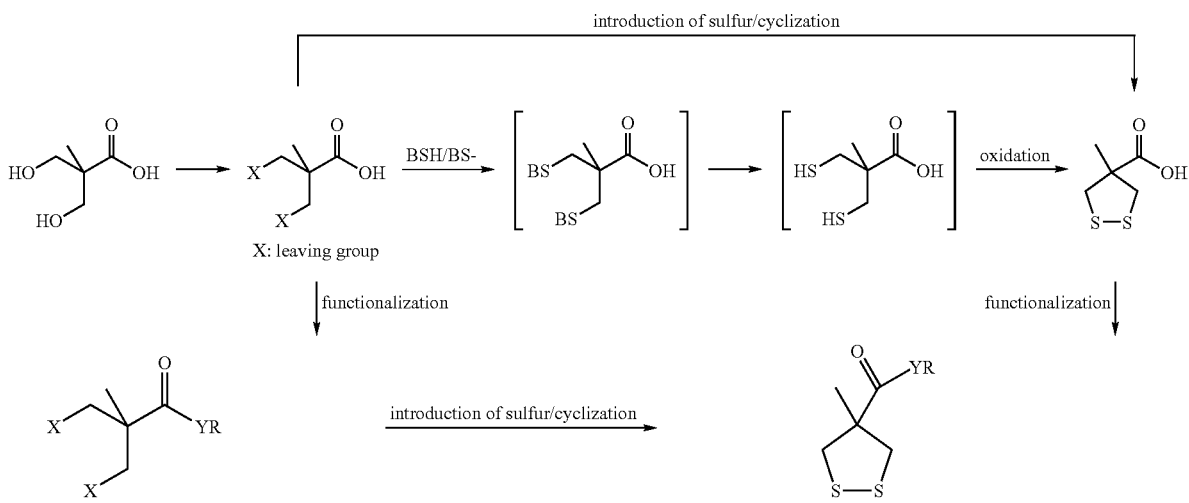

This introduction of sulfur may be performed:

(i) in a single step using a metal disulfide (for instance $Na_2S_2$) or tetrathiomolybdate salts in polar protic or aprotic solvents (for example water, DMF, methanol or acetonitrile) to give the dithiolane, (ii) or in two steps by forming a dithiol intermediate, which, in the presence of an oxidizing agent (oxygen, DMSO, $FeCl_3$, $I_2$, $Br_2$, sodium iodide, thallium trifluoroacetates, silver triflates, aqueous hydrogen peroxide solution, sodium iodate and periodate, sodium hypochlorite, potassium ferricyanide or chromium oxide) in neutral or basic medium, leads to the formation of the dithiolane. In this case, the dithiol is obtained by conversion (in basic or acidic medium) in a polar or apolar solvent of an intermediate species via derivatives of thioacetic acid $CH_3COSH$ (in the presence of base), with thiourea or NaSH, via the formation of dithiosulfonates (Bunte salts).

Functionalization of the carboxylic acid COOH into a function COYR may be performed according to the conventional acid activation methods (described in Comprehensive Organic Transformations by R. Larock, Wiley VCH Ed. in the chapter: Interconversion of nitriles, carboxylic acids and derivatives). Preferably, the methods used favor proceeding via the acid chloride (by using thionyl or oxalyl chloride, or 1-chloro-N,N,2-trimethyl-1-propenamine) or via the formation of a mixed anhydride (using alkyl chloroformates) or the use of carbodiimides or diethyl cyanophosphate (Phosphorus in organic synthesis—XI, Amino acids and peptides—XXI, Reaction of diethyl phosphorocyanidate with carboxylic acids. A new synthesis of carboxylic esters and amides, *Tetrahedron,* 32, 1976, 2211-2217).*

The solvents used may be polar or apolar, and protic or aprotic (for example toluene, dichloromethane, THF, DMF, acetonitrile, water, methanol or isopropanol).

All these reactions may be performed at temperatures of from −20 to 100° C.

The production of the products of oxidation of the sulfur atoms of the dithiolanes of formula (I) (n other than zero) may be performed according to the following reaction scheme:

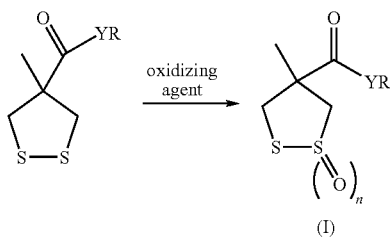

using oxidizing agents such as oxygen, hydrogen peroxide, DMSO, sodium periodate, organic peracids, inorganic persulfates or inorganic permanganates in the presence or absence of a catalyst (for example $Na_2WO_4$, $MoO_2Cl_2$ or trichlorooxobis(triphenylphosphine)rhenium). The various oxidation steps depend on the stoichiometry of the oxidizing agents used. The solvents that may be used may be water, acetone, dichloromethane or methanol.

These oxidations have been described in the following documents:

Oxidation of 1,2-Dithiolanes, Bernt Lindberg, Göran Bergson, Arkiv För Kemi, 1965, 23(31), 319-333;

Selective oxidation of sulfides to sulfoxides and sulfones at room temperature using $H_2O_2$ and an Mo(VI) salt as catalyst, Kandasamy Jeyakumar, Dillip Kumar Chand, *Tetrahedron Letters,* 47(2006), 4573-4576;

Rhenium-Catalyzed Oxidation of Thiols and Disulfides with Sulfoxides, Jeffrey B. Arterburn, Marc C. Perry, Sherry L. Nelson, Benjamin R. Dible, Mylena S. Holguin, *J. Am. Soc.,* 119, 9309-9310, 1997.

Advantageously, Compound 1 may be obtained according to the route described below starting with dichloropivalic acid according to a one-pot process, ending with a precipitation.

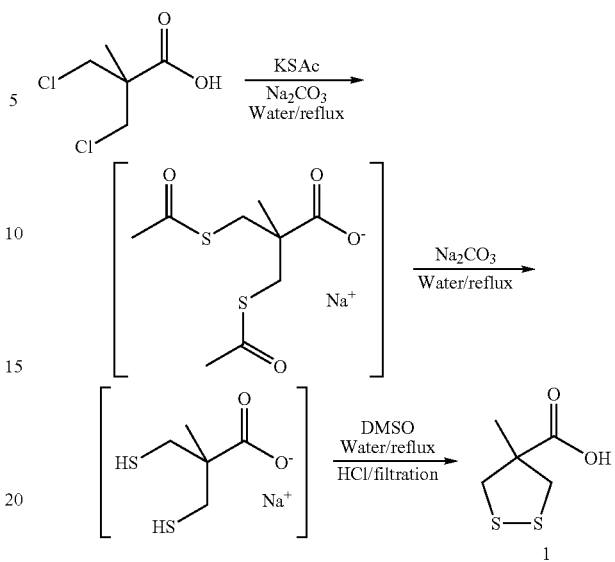

Advantageously, Compound 2 may be obtained from Compound 1, preferentially using isobutyl chloroformate or oxalyl chloride.

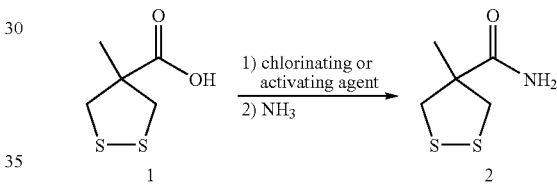

The compounds according to the invention are most particularly useful in the cosmetic or pharmaceutical field, in particular the dermatological field.

They may be present, alone or as a mixture, in cosmetic or pharmaceutical compositions, in an amount that may range from 0.01% to 10% by weight, preferably from 0.1% to 5% by weight and especially from 0.5% to 3% by weight relative to the total weight of the composition.

The compositions also comprise a physiologically acceptable medium, which will preferably be a cosmetically or pharmaceutically acceptable medium, especially a dermatologically acceptable medium, i.e., a medium that has no unpleasant odor, color or appearance, and that does not cause any unacceptable stinging, tautness or redness. In particular, the composition is suitable for topical application to the skin.

The term "physiologically acceptable medium" means a medium that is compatible with human keratin materials such as bodily or facial skin, the lips, mucous membranes, the eyelashes, the nails, the scalp and/or the hair.

The compositions according to the invention may then comprise any adjuvant commonly employed in the envisaged application field.

Exemplary are water; organic solvents, especially $C_1$-$C_6$ alcohols and $C_2$-$C_{10}$ carboxylic acid esters; carbon-based and/or silicone oils, of mineral, animal and/or plant origin; waxes, pigments, fillers, colorants, surfactants, emulsifiers, co-emulsifiers; cosmetic or dermatological active agents, UV-screening agents, polymers, hydrophilic or lipophilic gelling agents, thickeners, preservatives, fragrances, bactericides, ceramides, odor absorbers, antioxidants.

These optional adjuvants may be present in the composition in a proportion of from 0.001% to 80% by weight and especially from 0.1% to 40% by weight relative to the total weight of the composition. Depending on their nature, these adjuvants may be introduced into the fatty phase or into the aqueous phase of the composition, or into lipid vesicles. In any case, these adjuvants, and the proportions thereof, will be selected by one skilled in the art such that the advantageous properties of the compounds according to the invention are not, or are not substantially, adversely affected by the envisaged addition.

As active agents, it will be advantageous to introduce into the composition according to the invention at least one compound selected from among: desquamating agents; calmatives, organic or mineral photoprotective agents, moisturizers; depigmenting or propigmenting agents; anti-glycation agents; NO-synthase inhibitors; agents for stimulating the synthesis of dermal or epidermal macromolecules and/or for preventing their degradation; agents for stimulating fibroblast and/or keratinocyte proliferation or for stimulating keratinocyte differentiation; muscle relaxants and/or dermo-decontracting agents; tensioning agents; anti-pollution agents and/or free-radical scavengers; agents acting on the capillary circulation; agents acting on the energy metabolism of cells; and mixtures thereof.

Examples of such additional compounds are: retinol and derivatives thereof such as retinyl palmitate; ascorbic acid and derivatives thereof such as magnesium ascorbyl phosphate and ascorbyl glucoside; tocopherol and derivatives thereof such as tocopheryl acetate; nicotinic acid and precursors thereof such as nicotinamide; ubiquinone; glutathione and precursors thereof such as L-2-oxothiazolidine-4-carboxylic acid; plant extracts and especially plant proteins and hydrolysates thereof, and also plant hormones; marine extracts such as algal extracts; bacterial extracts; sapogenins such as diosgenin and wild yam extracts containing them; ceramides; hydroxy acids such as salicylic acid and 5-n-octanoylsalicylic acid; resveratrol; oligopeptides and pseudo-dipeptides and acyl derivatives thereof; manganese and magnesium salts, in particular the gluconates; and mixtures thereof.

The term "desquamating agent" means any compound capable of acting:

either directly on desquamation by promoting exfoliation, such as β-hydroxy acids, in particular salicylic acid and derivatives thereof (including 5-n-octanoylsalicylic acid); α-hydroxy acids, such as glycolic acid, citric acid, lactic acid, tartaric acid, malic acid or mandelic acid; urea; gentisic acid; oligofucoses; cinnamic acid; *Saphora japonica* extract; resveratrol;

or on the enzymes involved in the desquamation or degradation of corneodesmosomes, glycosidases, stratum corneum chymotryptic enzyme (SCCE) or other proteases (trypsin, chymotrypsin-like). Exemplary are agents for chelating mineral salts: EDTA; N-acyl-N,N'N'-ethylenediaminetriacetic acid; aminosulfonic compounds and in particular (N-2-hydroxyethylpiperazine-N-2-ethane)sulfonic acid (HEPES); 2-oxothiazolidine-4-carboxylic acid (procysteine) derivatives; derivatives of α-amino acids of glycine type (as described in EP-0,852,949, and also sodium methyl glycine diacetate marketed by BASF under the trade name Trilon M); honey; sugar derivatives such as O-octanoyl-6-D-maltose and N-acetylglucosamine.

The desquamating agents are generally present in the composition according to the invention in proportions ranging from 0.01% to 15% by weight and preferably ranging from 0.1% to 10% by weight relative to the total weight of the composition.

As calmatives that may be included in the composition according to the invention, exemplary are pentacyclic triterpenes and extracts of plants (e.g.,: *Glycyrrhiza glabra*) containing them, for instance β-glycyrrhetinic acid and salts and/or derivatives thereof (glycyrrhetinic acid monoglucuronide, stearyl glycyrrhetinate or 3-stearoyloxyglycyrrhetic acid), ursolic acid and its salts, oleanolic acid and its salts, betulinic acid and its salts, an extract of *Paeonia suffruticosa* and/or *lactiflora*, salicylic acid salts and in particular zinc salicylate, the phycosaccharides from the company Codif, an extract of *Laminaria saccharina*, canola oil, bisabolol and camomile extracts, allantoin, Sepivital EPC (phosphoric diester of vitamins E and C) from SEPPIC, omega-3 unsaturated oils such as musk rose oil, blackcurrant oil, ecchium oil, fish oil, plankton extracts, capryloylglycine, Seppicalm VG (sodium palmitoylproline and *Nymphea alba*) from SEPPIC, a *Pygeum* extract, an extract of *Boswellia serrata*, an extract of *Centipeda cunninghami*, an extract of *Helianthus annuus*, an extract of *Linum usitatissimum*, tocotrienols, extracts of *Cola nitida*, piperonal, an extract of clove, an extract of *Epilobium Angustifolium, Aloe vera*, an extract of *Bacopa monieri*, phytosterols, cortisone, hydrocortisone, indomethacin and betamethasone.

The calmatives are generally present in the composition according to the invention in proportions ranging from 0.01% to 15% by weight and preferably ranging from 0.1% to 10% by weight relative to the total weight of the composition.

The organic photoprotective agents are selected especially from among anthranilates; cinnamic derivatives; dibenzoylmethane derivatives; salicylic derivatives; camphor derivatives; triazine derivatives such as those described in U.S. Pat. No. 4,367,390, EP-863,145, EP-517,104, EP-570,838, EP-796,851, EP-775,698, EP-878,469, EP-933,376, EP-507, 691, EP-507,692, EP-790,243, EP-944,624; benzophenone derivatives; β,β-diphenylacrylate derivatives; benzotriazole derivatives; benzalmalonate derivatives; benzimidazole derivatives; imidazolines; bis-benzazolyl derivatives as EP-669,323 and U.S. Pat. No. 2,463,264; p-aminobenzoic acid (PABA) derivatives; methylenebis(hydroxyphenylbenzotriazole) derivatives as described in U.S. Pat. Nos. 5,237, 071, 5,166,355, GB-2,303,549, DE-197,26,184 and EP-893, 119; screening polymers and screening silicones such as those described especially in WO 93/04665; α-alkylstyrene-based dimers, such as those described in DE-198,55,649.

The mineral photoprotective agents may be selected especially from pigments or even nanopigments (mean size of the primary particles: generally from 5 nm to 100 nm and preferably from 10 nm to 50 nm) of coated or uncoated metal oxides, for instance nanopigments of titanium oxide (amorphous or crystallized in rutile and/or anatase form), of iron oxide, of zinc oxide, of zirconium oxide or of cerium oxide, which are all UV photoprotective agents that are well known per se. Standard coating agents are, moreover, alumina and/or aluminum stearate. Such coated or uncoated metal oxide nanopigments are described in particular in EP-518,772 and EP-518,773.

The photoprotective agents are generally present in the composition according to the invention in proportions ranging from 0.1% to 20% by weight and preferably ranging from 0.2% to 15% by weight relative to the total weight of the composition.

This compositions may be in any galenical form normally employed in the cosmetic or pharmaceutical field, and especially in the form of an optionally gelled aqueous or aqueousalcoholic solution, a dispersion, optionally a two-phase dispersion, of the lotion type, an oil-in-water or water-in-oil or multiple emulsion (for example W/O/W or O/W/O), an aqueous gel, a dispersion of oil in an aqueous phase with the aid of spherules, these spherules possibly being polymer nanoparticles such as nanospheres and nanocapsules or, better still, lipid vesicles of ionic and/or nonionic type; aqueous or oily gels. These compositions are prepared according to the usual methods. According to this invention, a composition in the form of an emulsion, especially an oil-in-water emulsion, is preferred.

The composition may be more or less fluid and may have the appearance of a white or colored cream, an ointment, a milk, a lotion, a serum, a paste, a gel or a mousse. It may optionally be applied in aerosol form. It may also be in solid form, in particular in the form of a stick.

When the composition is an emulsion, the proportion of the fatty phase may range from 5% to 80% by weight and preferably from 8% to 50% by weight relative to the total weight of the composition. The emulsifier and the co-emulsifier may be present in a proportion ranging from 0.3% to 30% by weight and preferably from 0.5% to 20% by weight relative to the total weight of the composition.

The composition according to the invention may constitute a skincare composition, and especially a cleansing, protecting, medicated or care cream for the face, the hands, the feet, the major anatomical folds or the body (for example day creams, night creams, makeup-removing creams, foundation creams or anti-sun creams); a fluid foundation, a makeup-removing milk, a protective or care body milk or an anti-sun milk; a skincare lotion, gel or mousse, such as a cleansing lotion.

To further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES OF SYNTHESIS

Example 1

Synthesis of 4-methyl-1,2-dithiolane-4-carboxylic Acid (Compound 1)

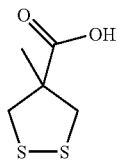

8 g of dichloropivalic acid are placed in a 250 ml three-necked flask on which are mounted a condenser and a dropping funnel. The acid is dissolved in 80 ml of water, and 4.6 g of $Na_2CO_3$ are slowly added. A solution of 10.7 g of potassium thioacetate is added dropwise, and the reaction medium is brought to reflux. 14.9 g of $Na_2CO_3$ are added and the medium is again refluxed. After disappearance of the starting material, 7.3 ml of DMSO are added, followed by refluxing. The dithiolane is obtained after acidification by precipitating and drying the solid under vacuum. A pale yellow solid is obtained.

1H NMR (400 MHz, DMSO-d6): δ ppm 3.69 (d, 2H), 2.95 (d, 2H), 1.53 (s, 3H), ESI–: [(M, H)–]=163 m/z.

Example 2

Synthesis of Octyl 4-methyl-1,2-dithiolane-4-carboxylate (Compound 9)

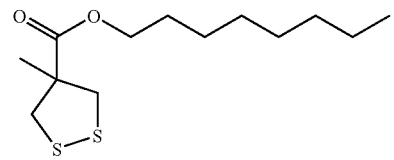 [SMILES: CCCCCCCCOC(=O)C1(C)CSSC1]

1 g of acid (24) and then 0.8 ml of 1-chloro-N,N,2-trimethylpropenylamine (27) are placed in 20 ml of dichloromethane in a 100 ml three-necked flask using a syringe. The mixture is stirred for 1 hour, followed by dropwise addition via an additional funnel to a reaction medium at −5° C. containing 1.28 ml of triethylamine, 0.96 ml of octanol and 20 ml of dichloromethane. The mixture is stirred. The reaction medium is then washed with water (3×30 ml). The aqueous phase is extracted with 3×10 ml of EtOAc. The combined organic phases are washed with 30 ml of saturated aqueous NaCl solution and then dried over $Na_2SO_4$, filtered and then concentrated under vacuum (500 mbar, T=40° C.) on a rotavapor. The crude product obtained is a yellow oil (m=1.25 g). Purification is performed by flash chromatography on a column of silica (m $SiO_2$=40 g, eluting with a 100/0 and then 98/2 heptane/EtOAc gradient).

After concentrating the fractions on a rotavapor (P=100 mbar, T=40° C.), 1.08 g of yellow oil are obtained.

Yield=66%; Rf (ester)=0.16 (eluent: cyclohexane);

1H NMR (400 MHz, DMSO-d6): δ ppm 4.08 (t, 2H), 3.57 (d, 2H), 3.02 (d, 2H), 1.58 (m, 2H), 1.40 (s, 3H), 1.29 (m, 10H), 0.86 (t, 3H) MS m/z (M+, 277; M+23, 299).

The following manipulations were performed under the same conditions described previously, with only the nucleophile varying.

Example 3

Synthesis of S-[2-(acetylamino)ethyl]-4-methyl-1,2-dithiolane-4-carbothioate (Compound 13)

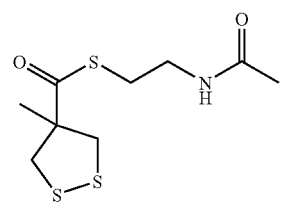

Method identical to that of Example 2: the nucleophile used is N-acetylcysteamine (0.64 ml).

Purification is performed by flash chromatography on a column of silica (m $SiO_2$=40 g; eluting with a linear gradient of 100/0 and then 98/2 DCM/MeOH).

After concentrating the fractions on a rotavapor (P=200 mbar, T=40° C.), 0.32 g of a mixture comprising the expected compound and N,N,2-trimethylpropionamide is obtained. After evaporating under vacuum, the expected final compound is obtained in the form of a thick yellow liquid. Yield=10%; Rf (expected)=0.3; eluent: 95/5 DCM/MeOH; 1H NMR (DMSO-d6): δ ppm 8.03 (t, NH), 3.57 (d, 2H), 3.18 (dt 2H), 3.10 (d, 2H), 2.96 (m, 2H), 1.79 (s, 3H), 1.43 (s, 3H); MS m/z (M+, 266; M+23, 288).

Example 4

Synthesis of N-(2-hydroxyethyl)-4-methyl-1,2-dithiolane-4-carboxamide (Compound 14)

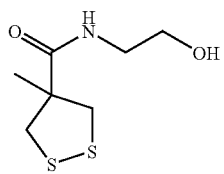

Method identical to that of Example 2: the nucleophile used is ethanolamine (0.36 ml). After filtering the reaction medium, a crude yellow oil is obtained (m=1.850 g).

Purification is performed by flash chromatography on a column of silica (eluting with a linear gradient of 100/0 and then 98/2 DCM/MeOH).

After concentrating the fractions on a rotavapor (P=500 mbar, T=40° C.), 800 mg of a yellow oil (pure compound) are obtained; yield=65%.

Rf (expected)=0.43; eluent: 9/1 DCM/MeOH; 1H NMR (DMSO-d6): δ ppm 7.80 (t, NH), 4.64 (t, OH), 3.53 (d, 2H), 3.40 (dt, 2H), 3.14 (m, 2H), 2.99 (d, 2H), 1.34 (s, 3H); MS m/z (M+, 208; M+23, 230).

Example 5

Synthesis of 4-methyl-1,2-dithiolane-4-carboxamide (Compound 2)

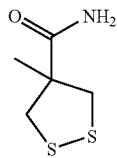

Method (Ex. 5-a) identical to that of Example 2: the nucleophile used is ammonia in isopropanol (9.5 ml). After filtering the reaction medium, a crude yellow oil is obtained (m=1.853 g).

Purification is performed by flash chromatography on a column of silica (eluent: DCM).

After concentrating the fractions on a rotavapor (P=600 mbar, T=40° C.), 500 mg of pure expected yellow solid are obtained. Yield=52%.

Alternatively, method (Ex. 5-b), 1.2 equivalents of isobutyl chloroformate are added, at 0° C., to a solution of 1 g of Compound 1 in THF with 1.2 equivalents of triethylamine. After 2 hours at room temperature, the reaction medium is added to a cooled solution of ammonia, either at 28% in water or at 2N in isopropanol. The medium is stirred at room temperature for the time required, and then concentrated under vacuum. The crude product is then taken up in toluene, to give Compound 2 after precipitation. Yield=60%

Rf (expected)=0.45; eluent: 95/5 DCM/MeOH; 1H NMR (DMSO-d6): δ ppm 7.38 (s, NH), 7.13 (s, NH), 3.53 (d, 2H), 2.97 (d, 2H), 1.34 (s, 3H); ESI–: [(M, H)–]=162 m/z; ESI+: [(M, Na)+]=186 m/z, ESI+: [(M, H)+]=164 m/z; ESI+: [(M, Na, MeOH)+]=218 m/z.

Example 6

Synthesis of N-(2,3-dihydroxypropyl)-4-methyl-1,2-dithiolane-4-carboxamide (Compound 15)

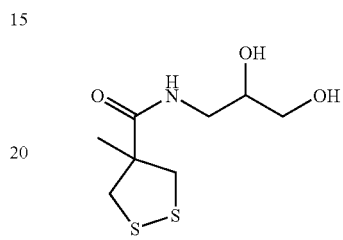

Method identical to that of Example 2: the amount of starting acid used is 0.25 g and the nucleophile used is dimethyldioxalanemethanamine (0.2 ml).

110 mg of pure expected yellow oil are obtained.

Yield=26%

Rf (expected)=0.51; eluent: 95/5 DCM/MeOH; 1H NMR (DMSO-d6): δ ppm 7.77 (t, 1H: NH), 3.55 (dd 4H, H3: diastereoisomers), 3.5 (m, 4H, H7: diastereoisomers), 3.20 (m, 2H, H8: diastereoisomers), 3.05 (dd, 2H: H9 and H9′), 2.99 (dd, 4H, H5), 1.35 (s, 12H, H10+H11: diastereoisomers), 0.9 (d, 3H, H6); MS m/z (M+23, 300).

70 mg of the pure product protected in acetonide form and about 5 g of Dowex resin are used in a solution of 3 ml of water and 2 ml of THF. The reaction mixture is stirred at room temperature for 20 hours and then at 40° C. for 40 hours.

The reaction medium with the resin is filtered under vacuum and washed with 3×10 ml of water and then 2×10 ml of EtOH. The filtrate is then concentrated on a rotavapor (P=200 mbar, T=40° C.). 30 mg of a yellow oil containing two diastereoisomers are obtained.

Rf (expected)=0.24; eluent: 9/1 DCM/MeOH; 1H NMR (DMSO-d6): δ ppm 7.80 (t, 1H: NH), 4.73 (d, OH), 4.50 (t, OH), 3.55 (d, 4H), 3.4 (m, 2H), 3.2 (m, 1H), 3.1 (m, 2H), 2.99 (d, 4H), 1.35 (s, 3H); MS m/z (M+, 208; M+23, 230).

Example 7

Synthesis of N-heptyl-4-methyl-1,2-dithiolane-4-carboxamide (Compound 10)

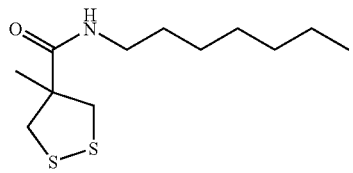 [SMILES: CCCCCCCNC(=O)C1(C)CSSC1]

Method identical to that of Example 2: the nucleophile is 0.22 ml of n-heptylamine.

The crude product obtained is a yellowish oil (m=0.27 g).

Purification is performed by flash chromatography on a column of silica (m SiO$_2$=12 g; eluent: 99/1 DCM/MeOH).

After concentrating the fractions on a rotavapor (P=500 mbar, T=40° C.), 0.21 g of a yellow oil (pure Compound 10) is obtained. Yield=54%.

Rf (expected)=0.5; eluent: 99/1 DCM/MeOH; 1H NMR (DMSO-d6): δ ppm 7.78 (t, NH), 3.53 (d, 2H), 3.1 (dt, 2H), 2.97 (d, 2H), 1.41 (tt, 2H), 1.34 (s, 3H), 1.23 (m, 8H), 0.85 (t, 3H); MS m/z (M+, 262; M+23, 284).

Example 8

Synthesis of Methyl 2-{[(4-methyl-1,2-dithiolan-4-yl)carbonyl]amino}-4-(methylsulfanyl)butanoate (Compound 12)

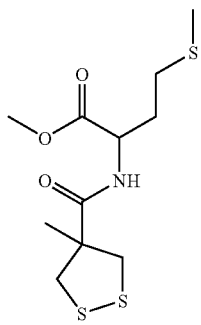

Method identical to that of Example 2: the nucleophile is L-methionine methyl ester. 140 mg of a yellow oil are obtained (7% yield).

1H NMR (DMSO-d6): δ ppm 8.13 (d, NH), 4.4 (m, 1H), 3.63 (s, 3H), 3.58 (m, 2H), 3.02 (m, 2H), 2.5 (m, 2H), 2.04 (s, 3H), 1.96 (m, 2H), 1.38 (s, 3H); MS m/z (M+, 310; M+23, 332).

Example 9

Synthesis of N-butyl-4-methyl-1,2-dithiolane-4-carboxamide (Compound 11)

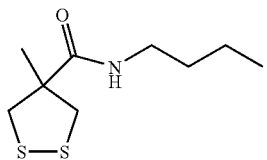

1.1 equivalents of triethylamine and 1 equivalent of diethyl cyanophosphate are added to 1 g of 1,2-dithiolane-4-methyl-4-carboxylic acid in ml of anhydrous THF, at 0° C. 1.1 equivalents of n-butylamine are added at 0° C. and the medium is stirred for 1 hour while warming to room temperature. After evaporation and aqueous work-up by extraction, the concentrated crude reaction product is purified on a column of silica (eluent: dichloromethane). After evaporating the fractions of interest, a yellow oil is obtained.

1H NMR (DMSO-d6): δ ppm 7.79 (t, NH), 3.53 (d, 2H), 3.1 (dt, 2H), 2.97 (d, 2H), 1.41 (tt, 2H), 1.34 (s, 3H), 1.23 (m, 8H), 0.85 (t, 3H); MS m/z (M+, 262; M+23, 284) 1H NMR (DMSO-d6): δ ppm 7.79 (t, NH), 3.54 (d, 2H), 3.08 (dt, 2H), 2.98 (d, 2H), 1.40 (q, 2H), 1.34 (s, 3H), 1.27 (m, 4H), 0.87 (t, 3H); ESI+: [(M, Na)+]=242 m/z.

Example 10

Synthesis of 4-methyl-1,2-dithiolane-4-carboxylic Acid 1-oxide (Compound 23)

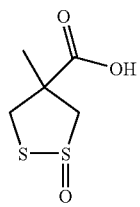

1 equivalent of aqueous 30% hydrogen peroxide solution is added to 100 mg of 4-methyl-1,2-dithiolane-4-carboxylic acid in 2 ml of acetone. The reaction medium is stirred at 20° C. overnight. After concentrating under vacuum, the thiosulfinate is obtained quantitatively in the form of a white solid as a mixture of two diastereoisomers in proportions of 70/30.

1H NMR (DMSO-d6): δ ppm major diastereoisomer: 4.38 (d, 1H), 3.78 (q, 2H), 3.11 (d, 1H), 1.57 (s, 3H) minor diastereoisomer: 4.36 (d, 1H), 3.96 (d, 1H), 3.42 (d, 1H), 3.31 (d, 1H), 1.51 (s, 3H)

13C NMR (DMSO-d6): δ ppm: 174.95; 174.63; 71.96; 70.85; 58.98; 56.73; 46.53; 45.03; 23.77; 21.96

ESI−: [(M, H)−]=179 m/z

Example 11

Synthesis of 4-methyl-1,2-dithiolane-4-carboxylic Acid 1,1-dioxide (Compound 24)

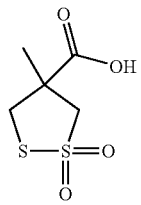

2 equivalents of aqueous 30% hydrogen peroxide solution and 0.15 equivalent of sodium tungstate Na$_2$WO$_4$ are added to 100 mg of 4-methyl-1,2-dithiolane-4-carboxylic acid in 2 ml of acetone. The reaction medium is stirred at 20° C. overnight. After filtering and concentrating under vacuum, the crude product is purified on a column of silica to give the thiosulfonate in the form of a white solid.

1H NMR (DMSO-d6): δ ppm 4.14 (d, 1H), 4.05 (d, 1H), 3.69 (d, 1H), 3.66 (d, 1H), 1.51 (s, 3H);

13C NMR (DMSO-d6): δ ppm 173.90; 65.86; 50.26; 44.58; 23.59

ESI−: [(M, H)−]=195 m/z

Example 12

Synthesis of Ethyl 4-methyl-1,2-dithiolane-4-carboxylate (Compound 4)

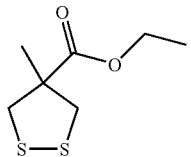

Sulfonic resin Dowex 50 WX8 (marketed by Aldrich) is added to 1 g of 4-methyl-1,2-dithiolane-4-carboxylic acid in 20 ml of ethanol. The mixture is refluxed for 24 hours and then filtered and evaporated to give the pure ethyl ester.

1H NMR (DMSO-d6): δ ppm 4.13 (q, 2H), 3.58 (d, 2H), 3.02 (d, 2H), 1.40 (s, 3H), 1.20 (t, 3H)
ESI+: [(2M, Na)+]=407 m/z

Example 13

Synthesis of Ethyl 4-methyl-1,2-dithiolane-4-carboxylate 1-oxide (Compound 25)

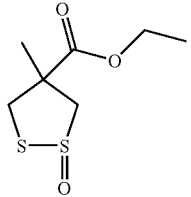

Oxidation of the ethyl ester is performed in the same manner as for the acid.

175 mg of a pale yellow oil are obtained.
1H NMR (DMSO-d6): δ ppm
major diastereoisomer: 4.4 (d, 1H), 4.11 (q, 2H), 3.8 (d, 1H), 3.75 (d, 1H), 3.17 (d, 1H), 1.59 (s, 3H), 1.53 (t, 3H)
minor diastereoisomer: 4.2 (d, 1H), 4.11 (q, 2H), 3.98 (d, 1H), 3.8 (d, 1H), 3.42 (d, 1H), 3.32 (d, 1H), 1.51 (s, 3H)
13C NMR (DMSO-d6): δ ppm 174.95, 174.63, 71.96, 70.85, 58.98, 56.73, 46.53, 45.03, 23.77, 21.96
ESI+: [(M, Na)+]=231 m/z; ESI+: [(M, Na, MeOH)+]=263 m/z; ESI+: [(2M, Na)+]=439 m/z
ESI+: [(M, Na)+]=231 m/z, ESI+: [(M, Na, MeOH)+]=263 m/z; ESI+: [(2M, Na)+]=439 m/z

Example 14

Synthesis of 4-methyl-1,2-dithiolane-4-carboxamide 1-oxide (Compound 26)

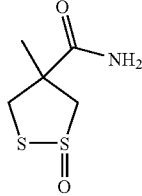

1 equivalent of aqueous 30% hydrogen peroxide solution is added to 100 mg of 4-methyl-1,2-dithiolane-4-carboxamide in 2 ml of acetone. The reaction medium is stirred at 20° C. overnight. After concentrating under vacuum and purifying on a column of silica, the thiosulfinate is obtained in the form of a white solid as a mixture of two diastereoisomers.

1H NMR (DMSO-d6): δ ppm
major diastereoisomer: 7.40 (bd, 2H), 4.31 (d, 1H), 3.78 (bs, 2H), 3.04 (d, 1H), 1.49 (s, 3H)
minor diastereoisomer: 7.32 (bd, 2H), 4.21 (d, 1H), 3.92 (d, 1H), 3.42 (d, 1H), 3.34 (d, 1H), 1.40 (s, 3H)
ESI−: [(M, H)−]=178 m/z

Example 15

Synthesis of 4-methyl-1,2-dithiolane-4-carboxamide 1,1-dioxide (Compound 27)

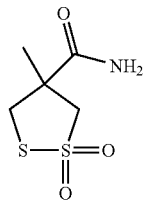

2 equivalents of aqueous 30% hydrogen peroxide solution and 0.15 equivalent of sodium tungstate Na$_2$WO$_4$ are added to 100 mg of 4-methyl-1,2-dithiolane-4-carboxamide in 2 ml of acetone. The reaction medium is stirred at 20° C. overnight. After filtering and concentrating under vacuum, the crude product is purified on a column of silica to give the thiosulfonate in the form of a white solid.

1H NMR (DMSO-d6): δ ppm 7.50 (bd, 2H), 4.21 (d, 1H), 4.08 (d, 1H), 3.66 (d, 1H), 3.59 (d, 1H), 1.49 (s, 3H);
ESI−: [(M, H)−]=194 m/z

Example 16

Synthesis of N-(4-hydroxy-3-methoxybenzyl)-4-methyl-1,2-dithiolane-4-carboxamide (Compound 16)

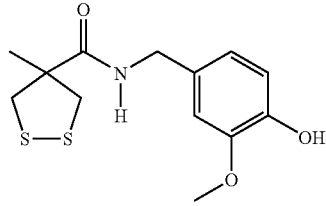 [SMILES: COc1cc(CNC(=O)C2(C)CSSC2)ccc1O]

24.3 mmol of N-hydroxysuccinimide are added to 24.3 mmol of dithiolane acid dissolved in 60 ml of dichloromethane cooled to 0° C. (on an ice bath). The reaction medium is stirred for 30 minutes at 0° C. A solution of 24.3 mmol of DCC in 50 ml of dichloromethane is added and the mixture is then stirred at 20° C. for 4 hours. The reaction medium is filtered and washed, and the filtrate is then evaporated to dryness on a rotavapor at 40° C. under vacuum to give 1-{[(4-methyl-1,2-dithiolan-4-yl)carbonyl]oxy}pyrrolidine-2,5-dione (m=7 g, quantitative yield). 10 ml of MeTHF, 3.16 mmol of 4-(aminomethyl)-2-methoxyphenol hydrochloride and 3.16 mmol of triethylamine are added to 1.58 mmol of 1-{[(4-methyl-1,2-dithiolan-4-yl)carbonyl]oxy}pyrrolidine- 2,5-dione. After stirring overnight, the mixture is filtered, rinsed with MeTHF and then evaporated. Flash chromatography, eluting with 98/2 dichloromethane/methanol, gives Compound 16 in the form of a yellow oil (84% yield).

1H NMR (DMSO-d6): δ ppm 1.39 (s, 3H); 3.03 (d, 2H); 3.56 (d, 2H), 3.63 (s, 3H, OCH₃), 4.21 (d, 2H), 6.64 (dd, 1H, Ar), 6.69 (d, 1H, Ar), 6.80 (d, 1H, Ar), 8.31 (t, 1H, NH), 8.79 (s, 1H, OH)

ESI+: [(M, H)+]=300 m/z

Example 17

Synthesis of N-[2-(4-hydroxy-3-methoxyphenyl) ethyl]-4-methyl-1,2-dithiolane-4-carboxamide (Compound 17)

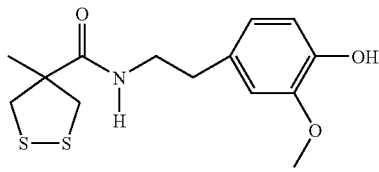

Same method as for Compound 16 with 4-(2-aminoethyl)-2-methoxyphenol hydrochloride. 320 mg of a yellow solid are obtained (yield=64%).

1H NMR (DMSO-d6): δ ppm 1.31 (s, 3H); 2.63 (t, 2H), 2.97 (d, 2H); 3.24 (m, 2H, NCH₂) 3.53 (d, 2H), 3.75 (s, 3H, OCH₃), 6.57 (dd, 1H, Ar), 6.67 (d, 1H, Ar), 674 (d, 1H, Ar), 8.86 (t, 1H, NH), 8.67 (s, 1H, OH)

ESI+: [(M, H)+]=314 m/z

Example 18

Synthesis of N,N-diethyl-4-methyl-1,2-dithiolane-4-carboxamide (Compound 18)

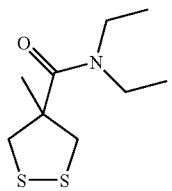

5 ml of anhydrous dichloromethane and 0.1 ml of anhydrous DMF are added to 2.26 mmol of Compound 1. The mixture is cooled to 0° C. and 2.7 mmol of oxalyl chloride are added. The mixture is stirred at 20° C. and then added at 0° C. to a mixture of 2.26 mmol of diethylamine, 5 ml of anhydrous dichloromethane and 6.8 mmol of diisopropylethylamine. The reaction medium is stirred for 3 hours at 20° C. When the reaction is complete, the medium is diluted in 50 ml of dichloromethane and then washed with 2×30 ml of water and 1×50 ml of saturated NH₄Cl solution, dried over Na₂SO₄ and evaporated to dryness on a rotavapor. After flash chromatography (eluent: heptane/EtOAc), Compound 18 is isolated in the form of a yellow oil (48% yield).

1H NMR (DMSO-d6): δ ppm 1.36 (s, 3H); 3.15 (d, 2H); 3.50 (d, 2H), 3.3 (m, 2×2H), 1.07 (m, 2×3H)

ESI+: [(M, H)+]=220 m/z

Example 19

Synthesis of Methyl 2-(acetylamino)-3-{[(4-methyl-1,2-dithiolan-4-yl)carbonyl]sulfanyl}propanoate (Compound 19)

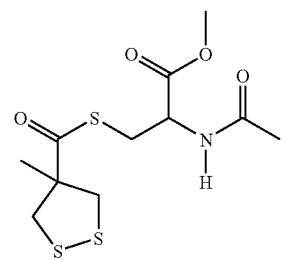 [SMILES: COC(=O)C(CSC(=O)C1(C)CSSC1)NC(C)=O]

Same method as in Example 18 with N-acetylcysteine methyl ester. 90 mg of a yellow oil are obtained (12% yield).

1H NMR (DMSO-d6): δ ppm 1.42 (s, 3H); 1.84 (s, 3H, OCH₃); 3.15 (d, 2H); 3.56 (d, 2H), 3.38-3.12 (dd, 2H), 3.65 (s, 3H, COCH₃), 8.42 (d, 1H, NH)

ESI+: [(M, H)+]=324 m/z

Example 20

Synthesis of S-(2-hydroxyethyl) 4-methyl-1,2-dithiolane-4-carbothioate (Compound 20)

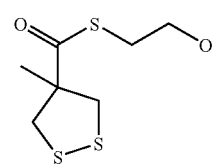

Same method as in Example 18 with sulfanylethanol. 130 mg of a yellow oil are obtained (26% yield).

1H NMR (DMSO-d6): δ ppm 1.43 (s, 3H); 3.1 (d, 2H); 3.56 (d, 2H), 2.99 (t, 2H: CH₂S), 3.48 (q, 2H: CH₂OH)

ESI+: [(M, Na)+]=247 m/z

Example 21

Synthesis of Ethyl {[(4-methyl-1,2-dithiolan-4-yl) carbonyl]sulfanyl}acetate (Compound 21)

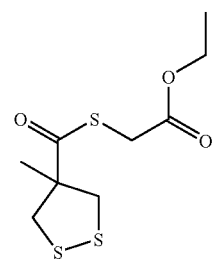

Same method as in Example 17 with ethyl thioglycolate. 30 mg of a virtually colorless oil are obtained (7% yield).

1H NMR (DMSO-d6): δ ppm 1.53 (s, 3H); 1.28 (t, 3H), 2.99 (d, 2H); 3.65 (d, 2H), 3.71 (s, 2H, SCH$_2$), 4.20 (q, 2H)

Example 22

Synthesis of [(4-methyl-1,2-dithiolan-4-yl)carbonyl]pyrrolidine (Compound 22)

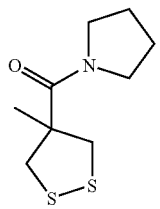

Same method as for Example 5-b with pyrrolidine. 130 mg of a yellow solid are obtained (38% yield).
1H NMR (DMSO-d6): δ ppm 1.36 (s, 3H); 1.81 (m, 2×2H); 3.10 (d, 2H); 3.30 (m, 2×2H); 3.58 (d, 2H),
ESI+: [(M, H)+]=218 m/z Example 23

Synthesis of 4-methyl-N-(1-methylethyl)-1,2-dithiolane-4-carboxamide (Compound 28)

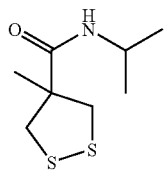

Same method as in Example 18 with isopropylamine. 250 mg of a beige-colored solid are obtained (54% yield).
1H NMR (DMSO-d6): δ ppm 1.06 (d, 2×3H); 1.33 (s, 3H, Hc); 2.99 (d, 2H, Hb); 3.56 (d, 2H, Ha); 3.88 (m, 1H),
ESI+: [(M, H)+]=206 m/z Example 24

Synthesis of 4-methyl-N-phenyl-1,2-dithiolane-4-carboxamide (Compound 29)

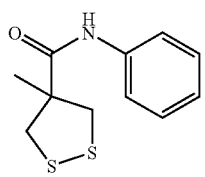

Same method as in Example 18 with aniline. 380 mg of a yellow oil are obtained (70% yield).
1H NMR (DMSO-d6): δ ppm 1.51 (s, 3H, Hc); 2.99 (d, 2H, Hb); 3.75 (d, 2H, Ha), 7.08 (t, 1H, Ar), 7.3 (t, 2H, Ar), 7.60 (d, 2H, Ar), 9.56 (s, 1h, NH)
ESI+: [(M, H)+]=240 m/z Example 25

Demonstration of the Activity on Constitutive Melanogenesis

A biological test demonstrated the depigmenting activity of the compounds according to the invention. The modulatory effect of the compounds on constitutive melanogenesis was measured according to the method described in FR-A-2,734,825 and also in the article by Schmidt et al., *Anal. Biochem.*, 235(2), 1996, pp. 113-118. This test is performed on a co-culture of keratinocytes and melanocytes.

For the test compounds, the inhibitory activity on melanin synthesis was determined, by estimating the ratio of incorporation of thiouracil to the incorporation of leucine, relative to 100% of the control (the control corresponds to the test performed without test compound).

The results are collated in the following table:

|  | Cytotoxicity on a co-culture | Maximum Activity |
| --- | --- | --- |
| Compound 2 (Example 5) | 100 μM | −76% |
| Arbutin | Non-cytotoxic | −44% |
| Kojic acid | 100 μM | −30% |

The results obtained show that Compound 2 according to the invention has greater depigmenting action than arbutin and kojic acid.

Example 26

A bleaching facial care cream of oil-in-water emulsion type is prepared, comprising (weight %):

| Compound 2 (Example 5) | 2% |
| --- | --- |
| glyceryl stearate | 2% |
| Polysorbate-60 (Tween 60 from ICI) | 1% |
| stearic acid | 1.4% |
| triethanolamine | 0.7% |
| carbomer | 0.4% |
| liquid fraction of shea butter | 12% |
| perhydrosqualene | 12% |
| antioxidant | qs |
| fragrance, preservative | qs |
| water | qs 100% |

A similar composition is prepared with the compound of Example 9 (Compound 11) or of Example 14 (Compound 26).

Example 27

A skin depigmenting gel is prepared, comprising (weight %):

| Compound 2 (Example 5) | 2% |
| --- | --- |
| hydroxypropylcellulose (Klucel H from Hercules) | 1% |
| antioxidant | qs |
| fragrance, preservative | qs |
| isopropanol | 40% |
| water | qs 100% |

A similar composition is prepared with the compound of Example 15 (Compound 27).

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for depigmenting, lightening and/or bleaching a keratin substrate, comprising topically applying thereon a thus effective amount of a cosmetic composition which comprises at least one compound of formula (I):

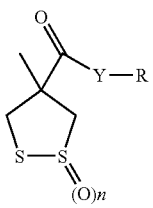

in which:

Y is O, $NR_1$ or S $R_1$ is a hydrogen atom; a saturated linear $C_1$-$C_{20}$ or branched $C_3$-$C_{20}$ or unsaturated $C_2$-$C_{20}$ alkyl hydrocarbon-based radical; a phenyl radical optionally substituted with one or more hydroxyl groups and/or with one or more $C_1$-$C_8$ alkoxy radicals;

R is a hydrogen atom; or a saturated linear $C_1$-$C_{20}$ or branched $C_3$-$C_{20}$ or unsaturated $C_2$-$C_{20}$ alkyl hydrocarbon-based radical, or a phenyl radical optionally substituted with one or more hydroxyl groups and/or with one or more $C_1$-$C_8$ alkoxy radicals, or a saturated $C_1$-$C_8$ alkyl radical containing a phenyl substituent optionally substituted with one or more hydroxyl groups and/or with one or more $C_1$-$C_8$ alkoxy radicals;

R optionally bears one or more substituents selected from the group consisting of $OR_2$, $SR_2$, $NR_2R_3$, $COOR_2$ in which:

$R_2$ is a hydrogen atom or a saturated linear $C_1$-$C_5$ or branched $C_3$-$C_5$ or unsaturated $C_2$-$C_5$ hydrocarbon-based radical, or a phenyl radical;

$R_3$ is a hydrogen atom, a saturated linear $C_1$-$C_5$ or branched $C_3$-$C_5$ or unsaturated $C_2$-$C_5$ hydrocarbon-based radical, a phenyl radical, or an acetyl radical;

with the proviso that when $Y=NR_1$, R and $R_1$ may together form a ring member selected from the group consisting of pyrrolidine, pyrroline, piperidine, piperazine, morpholine, thiomorpholine and azepine;

n=0 or 1 or 2;

or a salt, chelate, solvate or optional isomer thereof, formulated into a topically applicable, physiologically acceptable medium therefor.

2. The method as defined by claim 1, wherein formula (I):

Y is S, O, $NR_1$;

$R_1$ is a hydrogen atom, a saturated linear $C_1$-$C_{10}$ or branched $C_3$-$C_{10}$ alkyl hydrocarbon-based radical, R is a hydrogen atom, a saturated linear $C_1$-$C_{20}$ or branched $C_3$-$C_{20}$ alkyl hydrocarbon-based radical, a phenyl radical optionally substituted with one or more hydroxyl groups and/or with one or more $C_1$-$C_3$ alkoxy radicals, a saturated $C_1$-$C_5$ alkyl radical containing a phenyl substituent optionally substituted with one or more hydroxyl groups and/or with one or more $C_1$-$C_3$ alkoxy radicals; a linear $C_1$-$C_5$ alkyl hydrocarbon-based radical substituted with one or more identical or different groups selected from the group consisting of $OR_2$, $SR_2$, $NR_2R_3$, $COOR_2$ in which:

$R_2$ is a hydrogen atom or a saturated linear $C_1$-$C_5$ or branched $C_3$-$C_5$ or unsaturated $C_2$-$C_5$ hydrocarbon-based radical;

$R_3$ is a hydrogen atom, a saturated linear $C_1$-$C_5$ or branched $C_3$-$C_5$ hydrocarbon-based radical; a phenyl radical, or an acetyl radical;

when $Y=NR_1$, R and $R_1$ may together form a pyrrolidine ring; and n=0 or 1 or 2.

3. The method as defined by claim 1, wherein formula (I):

Y is O or $NR_1$;

$R_1$ is a hydrogen atom; a saturated linear $C_1$-$C_{10}$ or branched $C_3$-$C_{10}$ alkyl hydrocarbon-based radical;

R is a hydrogen atom, a saturated linear $C_1$-$C_{10}$ or branched $C_3$-$C_{10}$ alkyl hydrocarbon-based radical; a phenyl radical optionally substituted with one or more hydroxyl groups and/or with one or more methoxy radicals; a saturated $C_1$-$C_3$ alkyl hydrocarbon-based radical containing a phenyl substituent optionally substituted with one or more hydroxyl groups and/or with one or more methoxy radicals, a linear $C_1$-$C_4$ alkyl hydrocarbon-based radical substituted with one or more identical or different groups selected from the group consisting of $OR_2$, $SR_2$, $NR_2R_3$, $COOR_2$ in which:

$R_2$ is a hydrogen atom or a saturated linear $C_1$-$C_5$ or branched $C_3$-$C_5$ hydrocarbon-based radical;

$R_3$ is a hydrogen atom, a saturated linear $C_1$-$C_5$ or branched $C_3$-$C_5$ hydrocarbon-based radical; and n=0 or 1 or 2.

4. The method as defined by claim 1, wherein formula (I):

Y is $NR_1$;

$R_1$ is a hydrogen atom, a saturated linear $C_1$-$C_4$ alkyl hydrocarbon-based radical;

R is a hydrogen atom, a saturated linear $C_1$-$C_{10}$ or branched $C_3$-$C_{10}$ alkyl hydrocarbon-based radical, a phenyl radical, a saturated linear $C_1$-$C_4$ alkyl radical substituted with a phenyl optionally substituted with one or more identical or different groups selected from the group consisting of OH, OMe, a linear $C_1$-$C_4$ alkyl hydrocarbon-based radical substituted with one or more identical or different groups selected from the group consisting of OH, NHAc, $SR_2$, $COOR_2$ in which $R_2$ is a hydrogen atom or a linear $C_1$-$C_4$ alkyl radical; and n=0 or 1 or 2.

5. The method as defined by claim 1, wherein formula (I):

Y is NH;

R is a hydrogen atom, a saturated linear $C_1$-$C_{10}$ or branched $C_3$-$C_{10}$ alkyl hydrocarbon-based radical, a phenyl radical, a saturated linear $C_1$-$C_4$ alkyl radical substituted with a phenyl optionally substituted with one or more identical or different groups selected from the group consisting of OH, OMe, a linear $C_1$-$C_4$ alkyl hydrocarbon-based radical substituted with one or more identical or different groups selected from the group consisting of OH, NHAc, $SR_2$, $COOR_2$ in which $R_2$ is a hydrogen atom or a linear $C_1$-$C_4$ alkyl radical; and n=0 or 1 or 2.

6. The method as defined by claim 1, wherein the compound of formula (I) is selected from the group consisting of:

4-methyl-1,2-dithiolane-4-carboxylic acid, 4-methyl-1,2-dithiolane-4-carboxamide, methyl 4-methyl-1,2-dithiolane-4-carboxylate, ethyl 4-methyl-1,2-dithiolane-4-carboxylate, propyl 4-methyl-1,2-dithiolane-4-carboxylate,
benzyl 4-methyl-1,2-dithiolane-4-carboxylate,
N-methyl-4-methyl-1,2-dithiolane-4-carboxamide,
{[(4-methyl-1,2-dithiolan-4-yl)carbonyl]amino}acetic acid,
octyl 4-methyl-1,2-dithiolane-4-carboxylate,
N-heptyl-4-methyl-1,2-dithiolane-4-carboxamide,
N-butyl-4-methyl-1,2-dithiolane-4-carboxamide,
methyl 2-{[(4-methyl-1,2-dithiolan-4-yl)carbonyl]amino}-4-(methylsulfanyl)butanoate,
S-[2-(acetylamino)ethyl]4-methyl-1,2-dithiolane-4-carbothioate,
N-(2-hydroxyethyl)-4-methyl-1,2-dithiolane-4-carboxamide,
N-(2,3-dihydroxypropyl)-4-methyl-1,2-dithiolane-4-carboxamide,
N-(4-hydroxy-3-methoxybenzyl)-4-methyl-1,2-dithiolane-4-carboxamide,
N-[2-(4-hydroxy-3-methoxyphenyl)ethyl]-4-methyl-1,2-dithiolane-4-carboxamide,
N,N-diethyl-4-methyl-1,2-dithiolane-4-carboxamide,
methyl 2-(acetylamino)-3-{[(4-methyl-1,2-dithiolan-4-yl)carbonyl]sulfanyl}propanoate,
S-(2-hydroxyethyl) 4-methyl-1,2-dithiolane-4-carbothioate,
ethyl {[(4-methyl-1,2-dithiolan-4-yl)carbonyl]sulfanyl}acetate,
[(4-methyl-1,2-dithiolan-4-yl)carbonyl]pyrrolidine,
4-methyl-1,2-dithiolane-1-oxo-4-carboxylic acid,
4-methyl-1,2-dithiolane-1,1-dioxo-4-carboxylic acid,
ethyl 4-methyl-1,2-dithiolane-1-oxo-4-carboxylate,
4-methyl-1,2-dithiolane-4-carboxamide 1-oxide,
4-methyl-1,2-dithiolane-4-carboxamide 1,1-dioxide,
4-methyl-N-(1-methylethyl)-1,2-dithiolane-4-carboxamide,
4-methyl-N-phenyl-1,2-dithiolane-4-carboxamide,
N-[2-(4-hydroxyphenyl)ethyl]-4-methyl-1,2-dithiolane-4-carboxamide,
N-propyl-4-methyl-1,2-dithiolane-4-carboxamide,
N-pentyl-4-methyl-1,2-dithiolane-4-carboxamide,
N-hexyl-4-methyl-1,2-dithiolane-4-carboxamide,
N-octyl-4-methyl-1,2-dithiolane-4-carboxamide,
N-propyl-4-methyl-1,2-dithiolane-4-carboxamide,
butyl 4-methyl-1,2-dithiolane-4-carboxylate,
isopropyl 4-methyl-1,2-dithiolane-4-carboxylate,
pentyl 4-methyl-1,2-dithiolane-4-carboxylate,
hexyl 4-methyl-1,2-dithiolane-4-carboxylate,
heptyl 4-methyl-1,2-dithiolane-4-carboxylate.

7. The method as defined by claim 6, wherein the compound of formula (I) is selected from the group consisting of:
4-methyl-1,2-dithiolane-4-carboxamide,
N-heptyl-4-methyl-1,2-dithiolane-4-carboxamide,
N-butyl-4-methyl-1,2-dithiolane-4-carboxamide,
4-methyl-1,2-dithiolane-4-carboxamide 1-oxide, and
4-methyl-1,2-dithiolane-4-carboxamide 1,1-dioxide.

8. The method as defined by claim 1, in which the compound of formula (I) is present, alone or as a mixture, in the composition in an amount ranging from 0.01% to 10% by weight, relative to the total weight of the composition.

9. The method as defined by claim 1, in which the composition comprises at least one adjuvant selected from the group consisting of: water; organic solvents, $C_1$-$C_6$ alcohols, $C_2$-$C_{10}$ carboxylic acid esters; carbon-based and/or silicone oils, of mineral, animal and/or plant origin; waxes, pigments, fillers, colorants, surfactants, emulsifiers, co-emulsifiers; cosmetic or dermatological active agents, UV-screening agents, polymers, hydrophilic or lipophilic gelling agents, thickeners, preservatives, fragrances, bactericides, ceramides, odor absorbers, antioxidants.

10. The method as defined by claim 1, in which the composition comprises at least one active agent selected from the group consisting of: desquamating agents; calmatives, organic or mineral photoprotective agents, moisturizers; depigmenting or propigmenting agents; anti-glycation agents; NO-synthase inhibitors; agents for stimulating the synthesis of dermal or epidermal macromolecules and/or for preventing their degradation; agents for stimulating fibroblast and/or keratinocyte proliferation or for stimulating keratinocyte differentiation; muscle relaxants and/or dermo-decontracting agents; tensioning agents; anti-pollution agents and/or free-radical scavengers; agents acting on the capillary circulation; agents acting on the energy metabolism of cells; and mixtures thereof.

11. The method as defined by claim 1, comprising the depigmenting, lightening and/or bleaching of human skin.

\* \* \* \* \*